United States Patent [19]

Ishikawa et al.

[11] 4,271,084

[45] Jun. 2, 1981

[54] GERMANIUM-CONTAINING ORGANIC POLYMER AND THE PROCESS FOR THE PRODUCTION OF THE SAME

[75] Inventors: Akira Ishikawa, Tokyo; Yukihito Ishida, Fujisawa; Shiro Ikegami, Funabashi; Hiroshi Satoh, Tokyo, all of Japan; Ryuichi Sato, 2310, Kamikoizumi, Oizumicho, Ora-gun, Gunma-ken, Japan; Setsuo Tomisawa, Tokyo; Shigeru Toyoshima, Tokyo, both of Japan

[73] Assignee: Ryuichi Sato, Gunma, Japan

[21] Appl. No.: 12,151

[22] Filed: Feb. 14, 1979

[30] Foreign Application Priority Data

Mar. 1, 1978 [JP] Japan ................................. 53-21992
Mar. 1, 1978 [JP] Japan ................................. 53-21993

[51] Int. Cl.³ ............................................. C07F 7/30
[52] U.S. Cl. ................................. 260/429 R; 424/287
[58] Field of Search ..................... 260/429 R; 424/287

[56] References Cited

U.S. PATENT DOCUMENTS

| | | | |
|---|---|---|---|
| 3,689,516 | 9/1972 | Asai et al. | 260/429 R |
| 3,812,167 | 5/1974 | Pahk | 260/429 R |
| 4,066,678 | 1/1978 | Sato et al. | 260/429 R |

OTHER PUBLICATIONS

Bailar et al., Comprehensive Inorganic Chemistry, Pergamon Press, N.Y., pp. 13–17 (1973), Chemical Abstracts 46, 7925b (1952).

*Primary Examiner*—Helen M. S. Sneed
*Attorney, Agent, or Firm*—Kane, Dalsimer, Kane, Sullivan and Kurucz

[57] ABSTRACT

Germanium-containing organic polymers are obtained by polymerizing 3-trichlorogermylpropionic acid obtained by reacting halogermanium-phosphoric acid complexes with acrylic acid. The polymers are markedly effective in mental diseases, disturbances in heart and vascular systems and are also effective against various cancers.

8 Claims, 10 Drawing Figures

FIG_5

(a)
Fibrosis (male, age:82)

(b)
30mg/day (orally), one month

(c)
two months

(d)
three months

Lung cancer (female, age: 70)
Before administration

(b)

30mg/day (orally), three months

GERMANIUM-CONTAINING ORGANIC POLYMER AND THE PROCESS FOR THE PRODUCTION OF THE SAME

BACKGROUND OF THE INVENTION

1. Field of the Invention

The present invention relates to germanium-containing organic polymers which possess important therapeutic effects as medicine.

2. Description of the Prior Art

In recent years, attention has been drawn to germanium-containing organic compounds in view of their pharmacological activities, which have been disclosed in Japanese Patent Publication No. 2964/74, Japanese Patent Application Laid Open No. 61431/73, Japanese Patent Publication Nos. 21855/71 and 2498/71, etc. The germanium-containing organic compound disclosed in these publications is a low molecular weight compound represented by the formula: $(GeCH_2CH_2COOH)_2O_3$

SUMMARY OF THE INVENTION

As a result of extensive investigations on the synthesis of germanium-containing organic compounds other than the low molecular weight compound represented by the formula:

drawn their attention to the pharmacological activities of the germanium-containing organic compound, the present inventors have found novel germanium-containing organic polymers and the process for the production thereof as well as their use as medicine.

The present invention is directed to a germanium-containing organic polymer represented by the formula:

$$(\equiv GeCH-CH-COZ)_n O_{1.5n} \quad \text{(III)}$$
$$\overset{A}{|} \overset{B}{|}$$

or

$$(-O-\underset{|}{\overset{OH}{Ge}}-\overset{A}{\underset{|}{CH}}-\overset{B}{\underset{|}{CH}}-COZ)_n \quad \text{(IV)}$$

wherein A is a hydrogen atom, an alkyl group having 1 to 3 carbon atoms, —COOH, —COOR (wherein R is an alkyl group having 1 to 3 carbon atoms), B is a hydrogen atom or an alkyl group having 1 to 3 carbon atoms; Z is a hydroxy group, an alkoxy group having 1 to 3 carbon atoms or an alkyl group having 1 to 3 carbon atoms; n is an integer greater than 3, inclusive.

Of the germanium-containing organic polymers represented by the formulae (III) and (IV), particularly preferred are those wherein A is a hydrogen atom, a methyl group, —COOH, B is a hydrogen atom or a methyl group; and Z is a hydroxy group, a methoxy group, an ethoxy group or a methyl group.

Further the present invention is directed to a process for producing the germanium-containing organic polymer represented by the formula (III) or (IV) which comprises reacting halogermanium-phosphoric acid complexes obtained by treating germanium dioxide with hypophosphorous acid or salts thereof in hydrohalogenic acid, with a compound (I) of the formula:

$$\overset{A}{\underset{|}{CH}}=\overset{B}{\underset{|}{C}}-COZ \quad \text{(I)}$$

wherein A is a hydrogen atom, an alkyl group having 1 to 3 carbon atoms, —COOH, —COOR (wherein R is an alkyl group having 1 to 3 carbon atoms), B is a hydrogen atom or an alkyl group having 1 to 3 carbon atoms; and Z is a hydroxy group, an alkoxy group having 1 to 3 carbon atoms or an alkyl group having 1 to 3 carbon atoms; particularly preferred are in the case where A is a hydrogen atom, a methyl group, —COOH, B is a hydrogen atom or a methyl group; and Z is a hydroxy group, a methoxy group, an ethoxy group or a methyl group, and then polymerizing the resulting compound (II) represented by the formula:

$$X_3Ge\overset{A}{\underset{|}{CH}}-\overset{B}{\underset{|}{CH}}-COZ \quad \text{(II)}$$

wherein A, B and Z have the same meanings as defined above, and X is a halogen atom.

DESCRIPTION OF THE PREFERRED EMBODIMENTS

Representative examples for preparing the compounds of the present invention are illustratively shown below.

In the reaction schemes (1), (2) and (3), A, B, X and Z have the same meanings as defined above, and the low molecular weight polymer and the high molecular weight polymer shown in the reaction schemes (3) and (4) are germanium-containing organic polymers represented by the formulae (III) and (IV) which are objective compounds of the present invention. Whether the objective compound is of high molecular weight polymer or of low molecular weight polymer is determined by the number of n, more simply, depending upon the solubility of the compound in water.

Based upon the reaction schemes (1), (2), (3) and (4) described above, the process for producing the compounds of the present invention is described below in detail.

Germanium dioxide is reduced with hypophosphorous acid or salts thereof (metal salts or ammonium salts are preferred), whereby the germanium atom becomes di-valent and germanium dihalide is formed. the germanium dihalide is in equilibrium with germanium hydrogen trihalide wherein the germanium atom takes tetravalence, in hydrohalogenic acid. It is believed that this germanium hydrogen trihalide would be in equilibrium with the dissociation form shown at the right end of the reaction scheme (1), in an aqueous solution (see reaction scheme (1)). It is likely that phosphoric acid would contribute to this equilibrium system, since this reaction solution is dluted with water to thereby isolate a halogermanium-phosphoric acid complex.

To the thus formed germanium reagent, a polarized unsaturated compound, i.e., a compound represented by the formula:

wherein A, B and Z have the same meanings as defined above, is added, then a white crystalline compound represented by the formula:

wherein A, B, X and Z have the same meanings as defined above, is formed in high yield (see the reaction scheme (2)). As described above, the halogermanium-phosphoric acid complex obtained in accordance with the reaction scheme (1) can be stably isolated and, accordingly, this complex can previously be prepared according to the reaction scheme (1), followed by isolation. When it is desired to proceed with the reaction of the reaction scheme (2), this complex is added to an organic solvent or water and the resulting mixture is treated with hydrogen halide. The resulting solution is reacted with the compound of the formula (I) to obtain the compound of the formula (II), alternatively.

The compound represented by the formula (II) is dissolved in acetone or other organic solvents miscible with water (e.g. ethanol, methanol, cellosolve, acetonitrile, tetrahydrofuran, dioxane, dimethoxyethane, digline, dimethylsulfoxide, dimethylformamide) and then water is added to the resulting solution to obtain a low molecular weight polymer which is one of the compounds of the present invention (see the reaction scheme (3)). In the reaction of the reaction scheme (3), in the case where organic solvents immiscible with water are employed in place of solvents miscible with water, the low molecular weight polymer is obtained by mixing and agitating with water. This low molecular weight polymer is relatively easily soluble in water.

When the water soluble low molecular weight polymer is suspended in a small amount of water and thd suspension is allowed to settle, the high molecular weight polymer which is another objective compound of the present invention is obtained (see the reaction scheme (4)). This high molecular weight polymer is sparingly soluble in water and differs from the low molecular weight polymer in its crystalline form.

Both the low molecular weight polymer and the high molecular weight polymer are compounds of the present invention, and are represented by the formula:

or

-continued wherein A, B, Z and n are the same as defined above. Determination of either the low molecular weight polymer or the high molecular weight polymer can be made by the number of n in the formulae above, more simply, depending upon the solubility in water.

It has been made apparent from the infrared absorption spectrum, x-ray diffraction spectrum of powders, and the like that the compounds in accordance with the present invention are novel compounds different from heretofore known compound:

The compounds of the present invention possess important therapeutic effects and exhibit marked effects in use for treating a variety of abnormal physiological symptoms as shown below.

In most cases, drugs have hitherto been expected to defend against pathogenic attack of exogenic nature, so that they act only upon exogenous pathogeny showing a common property. The substances according to the present invention exhibit wide therapeutic effects, since they remedy the endogenic factors in the organisms into normal state, what is to be considered for the reason of the medical applicabilities in very wide range almost inconceivable in the first glance.

The compounds of the present invention are administered through administration routes such as oral administration, intraveneous administration, subcutaneous administration, intramuscular administration, intrarectal administration, and the like.

These compounds are also used on the skin in a direct form such as ointment.

In the case of oral administration, a sufficient effect is achieved in the daily dose of 0.1 mg/kg/day to 150 mg/kg/day. A sufficient effect is also achieved in the daily dose of 0.02 mg/kg/day to 20 mg/kg/day in intravenous injection, and in the daily dose of 0.04 mg/kg/day to 30 mg/kg/day in subcutaneous as well as intramuscular injections. For rectal use and as ointment, a pharmaceutical preparation which comprises mixing the active ingredient with a variety of bases in a ratio of 0.1 to 5% is obtained.

BASIC STUDY OF THE COMPOUNDS OF THE INVENTION

Reduction of blood pressure in rats with spontaneous hypertension, normalization of heart weight and inhibition of mortality in animals caused by liver cancer were noted after administration of the compounds of the present invention.

(1) Inhibition of Mortality in Donryu Rats with Liver Cancer

Figure 1:
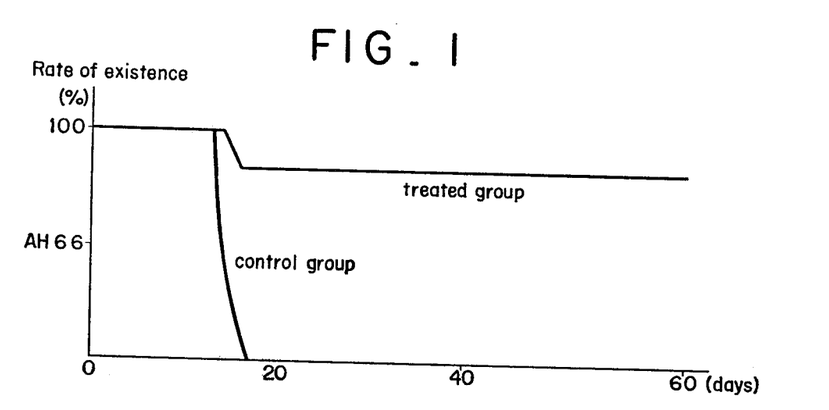
FIG. 1 indicates an effect of inhibition of the death of Donryu rats due to liver cancer when administered with the compounds of the invention.

AH-66 strain of ascites liver cancer was incubated in the veins of Donryu rats. The compounds of the present invention were orally administered in the daily dose of 100 mg/kg for consecutive 10 days following the third day of the incubation. Death caused by liver cancer was obviously inhibited as shown in FIG. 1.

(2) Effect on Rats with Spontaneous Hypertension

The compounds were orally given to rats with spontaneous hypertension over 4 consecutive months at the daily dosage of 100 mg/kg. Blood pressure was examined 7 months after. Then, the rats were sacrified to weigh the heart.

Figure 2:
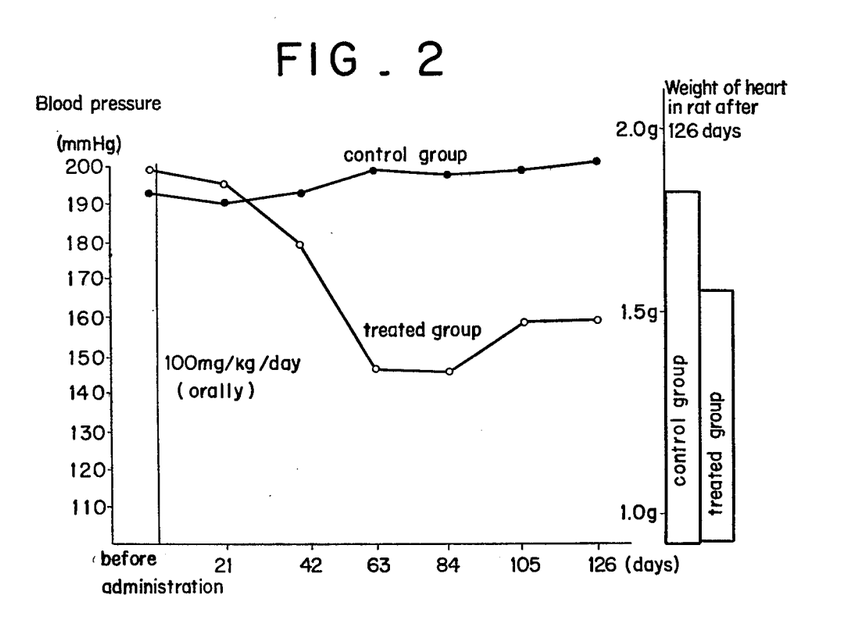
FIG. 2 indicates an effect of the compounds of the invention in rats of spontaneous hypertension.

The results are shown below (see Table 1 and FIG. 2).

(a) No difference in blood pressure between the control group and the medicated group was noted before the initiation of the test.

(b) Blood pressure in the medicated group was obviously lower than that of the control group after administration for 126 days.

(c) Comparing heart weight at the 126th day, the heart weight of the medicated group was clearly lighter than that of the control group.

EXAMPLES OF TREATMENT (1) Psycho-neurological Area

Epilepsy: (6 our of 8 cases were effective.)

A violent attack could be prevented by administration of the high molecular weight polymer (B) obtained in Example 3 in the dose of 90 mg/day. In addition, the amount of other anti-spasmodic agents could be reduced. In electroencephalogramic examination, the polymer possessed an effect of making spike waves characteristic of epilepsy disappear. What is specifically noted in the polymer is that it has no hypnotic tendency.

In a minor attack, the administration of the polymer (B) at the dose of 30 mg/day resulted in reduction of attack waves in electroencephalogram to ⅓ or less and could decrease yawn attacks.

Depressive Response (7 out of 10 cases were effective.)

By use in combination of the low molecular weight polymer (A) obtained in Example 2 with other antidepressants a marked synergistic effect on depressive response was noted.

Schizophrenia (8 out of 11 cases were effective.)

It was necessary to use the compounds of the invention in combination with other tranquilizers when symptoms were severe. However, by administration of the low molecular weight polymer (A) at the dose of 30 to 90 mg/day after the acute stage had passed, autopsychic disturbances and delusions could be completely suppressed.

Asthenis, Neurosis and Apocamnosis (including asthenopia):

18 out of 25 cases were effective at the dose of 30 mg/day. Vision was recovered by the administration of the compounds of the invention.

(2) Metabolic Disturbance

An effect of rendering fat dysbolism and sugar dysbolism normal was noted.

(3) Heart and Vascular System

Hypertension:

Patients with essential hypertension were given the low molecular weight polymer (A) at the dose of 30 to 40 mg/body/day. Reduction in maximum and minimum blood pressures were noted in 6 out of 10 cases after 10–25 days.

Angina Pectoris:

Patients who were not responsive to nitroglycerine or derivatives thereof, or who were strongly sensitive to its side effects received the low molecular weight polymer (A) at the dose of 30 mg/body/day. Attacks of angina pectoris, e.g., work-potential angina pectoris, were reduced and load electrocardiogram was also improved in 14 out of 19 cases. Subjective symptoms, of course, disappeared. The compounds of the invention could be administered in combination with other agents. Also no appereciable side effects were recognized.

Cardiovascular Distrubance:

The low molecular weight polymer (A) was orally given at the dose of 30 mg/body/day or 60 mg/body/day three times daily. Rhythmic abnormality was normalized in 13 out of 17 cases. When medication was discontinued, rhythmic abnormality was again observed in EKG, but improved by re-medication.

Antihemorrhagic Activity:

The administration of the low molecular weight polymer (A) was very effective against simple subcutaneous hemorrhage or senile subcutaneous hemorrhage, etc. (all 3 cases were effective).

Measurements of plasma plasmin, SK-activated plasma plasmin activator and plasminogen inhibitor indicated that the compounds of the invention possessed an effect of normalizing abnormal values of these respective measurements.

(4) Digestive Organ

An apocatastatic effect of ulcer in the digestive tract and an effect of controlling colonic functions were noted. In addition, medication with the low molecular weight polymer (A) at the dose of 30 mg/day was effective against chronic obstipation and diarrhae.

(5) Skin Disease

Due to the normalization of internal state, control of viruses entered in the living body is effected by these substances. According to experiments, it has been approved that induction of interferon was attained. This may be the cause that these substances are effective not only for various dermatic and general viral diseases but also for malignant tumor. The reason that they are effective for treating hepathopathy and nephropathy may also be attributed to the above fact.

Juvenile Verruca Planus:

By orally administering the low moleclar weight polymer (A) at the dose of 30 mg/body/day, 6 out of 8 cases healed completely in from 7 days to 3 months after.

Verruca Vulgaris:

By administration of the low molecular weight polymer (A) at the dose of 30 mg/body/day, 4 out of 5 cases completely healed in 28 to 42 days.

Infectious Molluscum Contagiosum:

By administration of the low molecular weight polymer (A) at the dose of 30 mg/body/day, 2 out of 4 cases completely healed in from 14 days to 1 month.

Herpes Zoster:

When administered with the low molecular weight polymer (A) at the dose of 30 mg/body/day, 3 out of 4 cases abortively healed completely.

According to fundamental experiment, and activation of macrophage is caused by these substances, whereby various allergic states can be improved. Moreover, since they offer metabolic improvement, marked effects on various psychoses, diabetes mellitus, autointoxication and cataract etc. can be attained.

(6) Allergic Disease

Bronchial Asthma:

Side effect or danger due to administration of adrenal corcical hormone in a large dosage can be prevented. If the compounds of the invention are given before onset of asthmatic attack, it is unnecessary to use adrenal cortical hormone. Alternatively, if, after filling the immediate needs with adrenal cortical hormone, the hormone is replaced by the compounds of the present invention, progression could take a sufficiently favorable turn. It is interesting that no side effects are seen.

Toxic Eruption, Urticaria and Collagenic Disease:

The low molecular weight polymer (A) was effective in 8 out of 12 cases. The polymer is a very valuable medicine particularly against severe collagenic diseases since it enables administration for a long period of time. Administration at the dose of 60 mg/day at an acute state and at the dose of 30 mg/day after the acute stage is sufficiently effective.

(7) Renal Disfunction

The compounds of the present invention are effective in patients who are not improved by administration of other diuretics. It is advantageous that no ill balance in salts is encountered. In the case of chronic nephrotic nephritis, decrease in urine protein can also be expected. The compounds of the present invention are also effective to patients who are just before artificial dialysis therapy. By administration of the low molecular weight polymer (A) at the dose of 30 mg/day, subjective symptoms, e.g., enervation, sensation of chest compression and headache, are improved. When edema on the back of the hand is not completely removed even though patients with heart failure receive cardiotonic diuretics, edema disappears when additionally administered with the compounds of the present invention at the dose of 30 mg/day. Ascites associated with liver cirrhosis and hydrothorax associated with heart failure also compretely regress.

(8) Disturbance in Liver Function

Symptoms in acute and chronic heptatitis, liver cirrhosis, fatty liver and liver cancer are improved.

(9) Disease in Obstetrical and Pediatric Areas

Success of treatment is noted in disturbance in nutritional metabolysis during pregnancy and lactation, hypoplasia, premature birth retinitis and autointoxication.

(10) When administered with the compounds of the invention at the dose of at least 60 to 90 mg in combination with other drugs which are given over a long period of time, side effects encountered by the other drugs are reduced, or synergistic effects with the other drugs are noted.

(11) Fibrosis

Markedly effective examples are noted in senile palindromic localized pneumonia. Capability of the compounds of the present invention in the retrogression of fibrosis is conspicuous.

Figure 9:
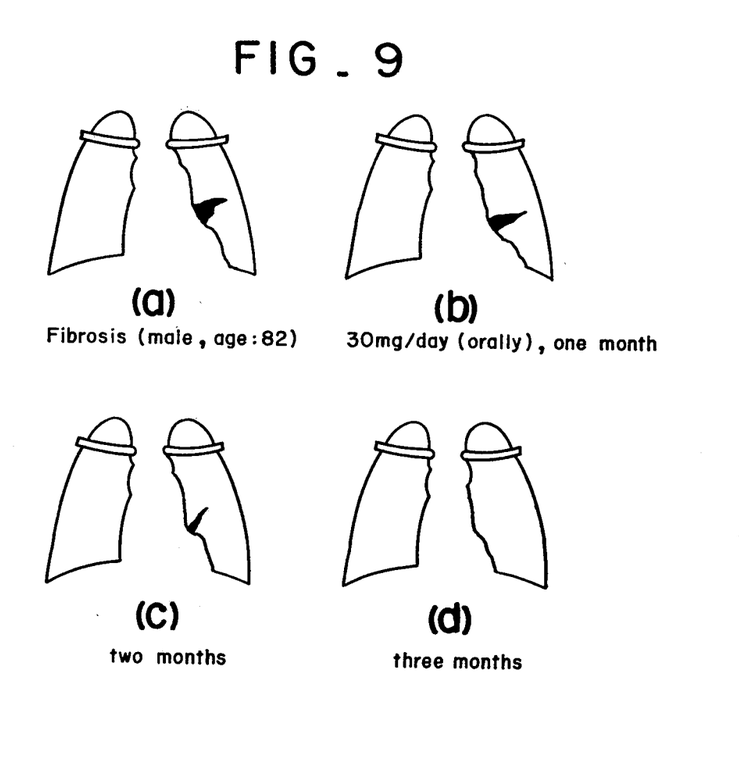
FIG. 9 represents a drawing showing the disappearance of fibrosis in a patient with senile palindromic localized pneumonia.

In FIG. 9, mammograms are illustratively shown; (a) is before administration of the low molecular weight polymer (A); the mammogram (b) is one month after the medication; (c) is two months after and (d) is three months after; per os at the dose of 30 mg/day. In (b) and (c), a tendency of complete retrogression of fibrosis was noted. Fibrosis completely retrogressed in (d).

(12) Cancer

By medication with the low molecular weight polymer (A), lung cancer was improved in the two given cases, mammarian cancer in the one given case, uterus cancer in 1 out of 3 cases, gastric cancer in 1 out of 3 cases and nasopharyngeal cancer in the two given cases.

Figure 10:
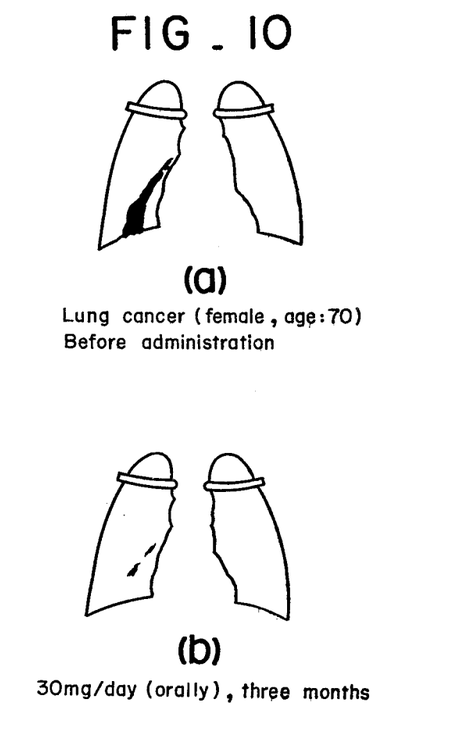
FIG. 10 represents a drawing showing an example in which metastatic lung cancer was treated.

FIG. 10 illustratively shows roentogenograms repesenting a healed example of metastatic lung cancer; wherein (a) is before medication and (b) is after medication with the compounds of the invention at the dose of 30 mg/day.

As are clearly seen from these illustrative roentogenograms, there is a tendency of fibrosis retrogression, a tendency of retrogression in density at the lower edge of the right pleura, and a normal proper curve of the diaphragm were observed.

(13) Opthalmological Area

Cataract:

One patient received eye wash five times daily with a 1% eye drop of the compounds of the invention, and at the same time, received orally the dosage of 30 mg/day three times daily. Another 10 patients received eye bath therapy (iontophoresis) with a 1% eye drop of the compounds of the present invention once a day and eye wash five times daily, and simultaneously orally received the 60 mg/day dosage three times daily. In both two groups, prevention of progress in the cataracts and recovery in vision were observed for all 11 patients.

Preparation of the compounds of the present invention will be described in detail with reference to the examples below.

EXAMPLE 1

Preparation of 3-trichlorogermylpropionic acid from germanium dioxide:

In 600 ml. of conc. hydrochloric acid was suspended 104.6 g. (1 mol) of germanium dioxide. To the resulting suspension was added 160 ml. (1 mol as the minimum titer) of 50% hypophosphorous acid solution while stirring. The reaction mixture was heated under reflux for about 3 hrs. while stirring to become a transparent solution, all being dissolved therein. With the addition of 72 g. (1 mol) of acrylic acid to the solution under agitation, heat generated. Since the reaction was exothermic, the whole amount of acrylic acid was added at such a rate that the reaction temperature did not exceed 50° C. When almost a half amount of acrylic acid was dropwise added, crystals were deposited from the reaction solution by adding a seed for crystallization, etc., which was advantageous. After adding the whole amount of acrylic acid, stirring was continued for further 0.5 to 1 hr. After cooling, the crystals were taken by suction-filtration, followed by drying under reduced pressure. Alternatively, wet crystals were dissolved in ether, methylene chloride, chloroform, benzene, etc. Thereafter, the solution was dried over a drying agent such as $MgSO_4$, etc. and the solvent was distilled off to obtain the crystals. As such, 227 g. (90% in yield) of white crystals were obtained. By recrystallization from n-hexane, white needles were obtained. The melting point thereof was 83.5°–86° C. which was identical with that in the literature. Also, elemental analysis, infrared absorption spectrum and NMR spectrum supported the structure of 3-trichlorogermylpropionic acid.

In addition, also in the case where metal salts or ammonium salts of hypophosphorous acid were employed in lieu of hypophosphorous acid, 3-trichlorogermylpropionic acid was similarly obtained.

Further, also in the case where other unsaturated compounds represented by the formula (I) were employed in lieu of acrylic acid, the corresponding compounds represented by the formula (II) were obtained as shown in the table below.

| Starting Material (Compound of the formula (I)) | Product (Compound of the formula (II)) | Yield (%) |
|---|---|---|
| $CH_2=CHCOOC_2H_5$ | $Cl_3GeCH_2CH_2COOC_2H_5$ | 70 |
| $CH_2=CCOOH$<br>$\quad\vert$<br>$\quad CH_3$ | $Cl_3GeCH_2CHCOOH$<br>$\qquad\qquad\vert$<br>$\qquad\qquad CH_3$ | 79 |
| HOOCCH=CHCOOH | COOH<br>$\vert$<br>$Cl_3GeCHCH_2COOH$ | 68 |
| $CH_3CH=CHCOOH$ | $CH_3$<br>$\vert$<br>$Cl_3GeCHCH_2COOH$ | 88 |
| $CH_2=CHCOCH_3$ | $Cl_3GeCH_2CH_2COCH_3$ | 60 |

EXAMPLE 2

Figure 3:
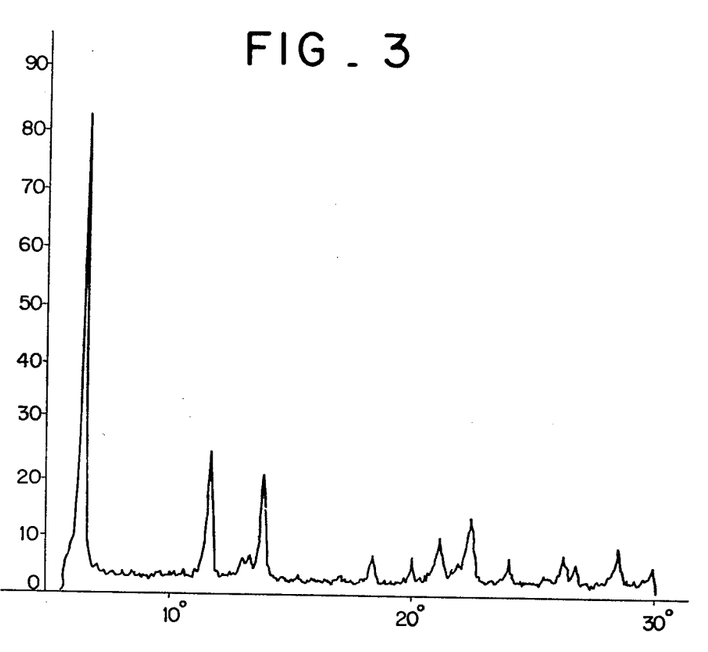
FIG. 3 indicates x-ray diffraction spectrum of water-soluble low molecular weight polymer (A) in a powdery form which is a compound in accordance with the present invention.
Figure 5:
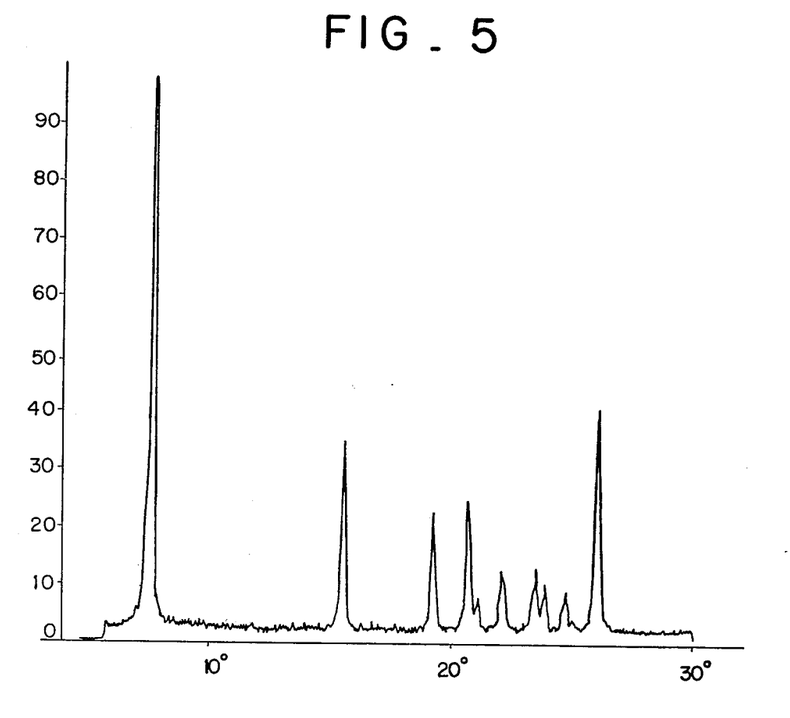
FIG. 5 represents an x-ray diffraction spectrum of the germanium-containing organic compound (GeCH$_2$CH$_2$COOH)$_2$O$_3$ described in Japanese Patent Publication No. 2964/74.
Figure 6:
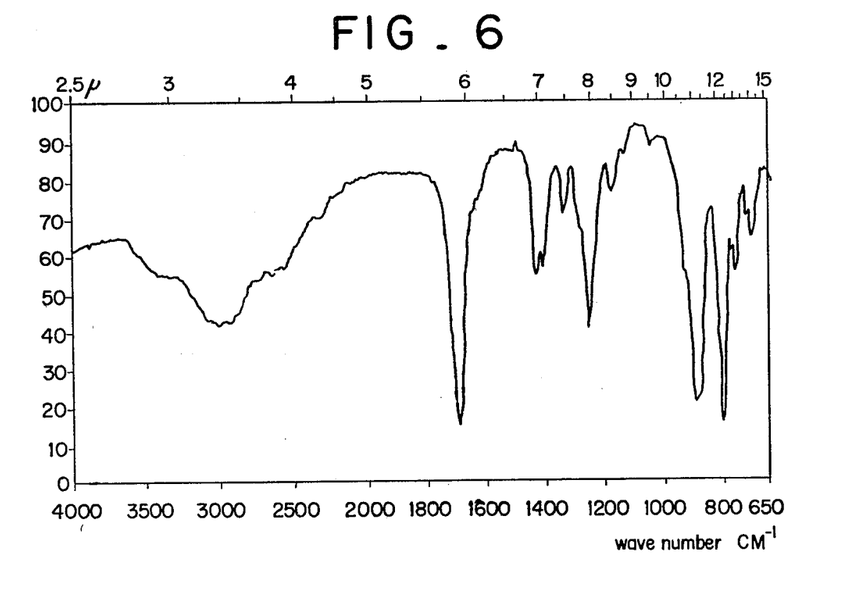
FIG. 6 represents an infrared absorption spectrum of a water-soluble low molecular weight polymer (A) which is a compound in accordance with the present invention.
Figure 8:
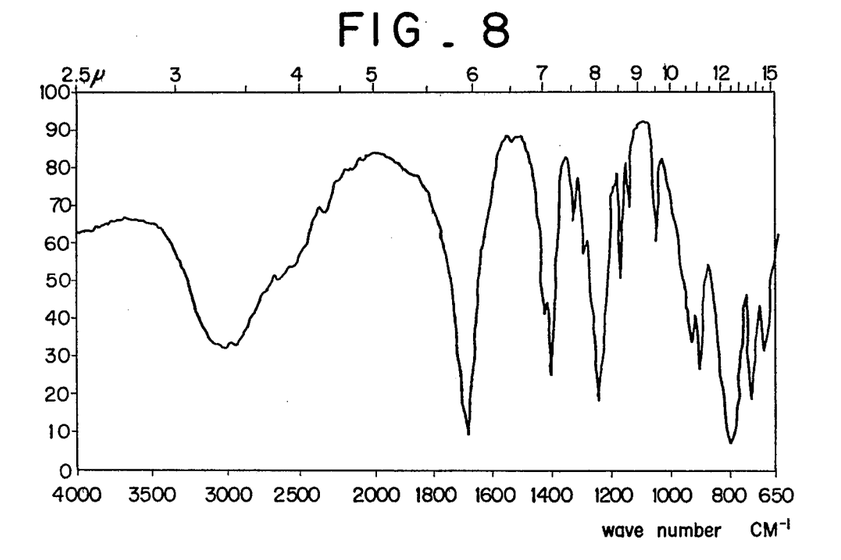
FIG. 8 represents an infrared absorption spectrum of (GeCH$_2$CH$_2$COOH)$_2$O$_3$ described in Japanese Patent Publication No. 2964/74.

Preparation of a low molecular weight polymer (A) of 3-oxygermylpropionic acid:

In 1.3 l. of acetone, a solvent compatible with water, was dissolved 252 g. (1 mol) of 3-trichlorogermylpropionic acid. To the solution, 1.3 l. of water was added with stirring. White hairy crystals were precipitated out. The reaction liquid was allowed to stand overnight. Then, crystals were collected by suction-filtration. The so obtained crystals were washed with acetone sufficiently, followed by drying under reduced pressure. White needle-like low molecular weight polymer (A) was obtained in an amount of 144 g. (85% in yield). In addition, also in the case where other solvents which are miscible with water (e.g., ethanol, methanol, cellosolve, acetonitrile, tetrahydrofuran, dioxane, dimethoxyethane, diglime, dimethylsulfoxide, dimethylformamide, etc.) are employed in place of acetone, the low molecular weight polymer (A) can also be obtained likewise. Furthermore, the low molecular weight polymer (A) can also be obtained using solvents which are immiscible with water (e.g., chloroform, methylenechloride, carbon tetrachloride, benzene, ether, etc.). In this case, the low molecular weight polymer (A) was precipitated out when a solution of 3-trichlorogermylpropionic acid was throughly shaked with water. Crystals of this low molecular weight polymer (A) neither decompose nor melt at temperatures below 320° C. It is found that the polymer differs from the germanium-containing organic compound prepared in accordance with the method described in Japanese Patent Publication No. 2964/71 since infrared absorption spectrum and x-ray diffraction spectrum of powders are completely different (compare FIGS. 3 and 6 showing x-ray diffraction spectrum of powders and infrared absorption spectrum as to the low molecular weight polymer (A) in accordance with the present invention, with FIGS. 5 and 8 showing powder x-ray diffraction spectrum and infrared absorption spectrum of the germanium-containing organic compound prepared in accordance with the method of Japanese Patent Publication No. 2964/71). In addition, the low molecular weight polymer (A) was relatively easily soluble in water and the solubility in water was about 1 g./100 ml. (25° C.).

EXAMPLE 3

Figure 4:
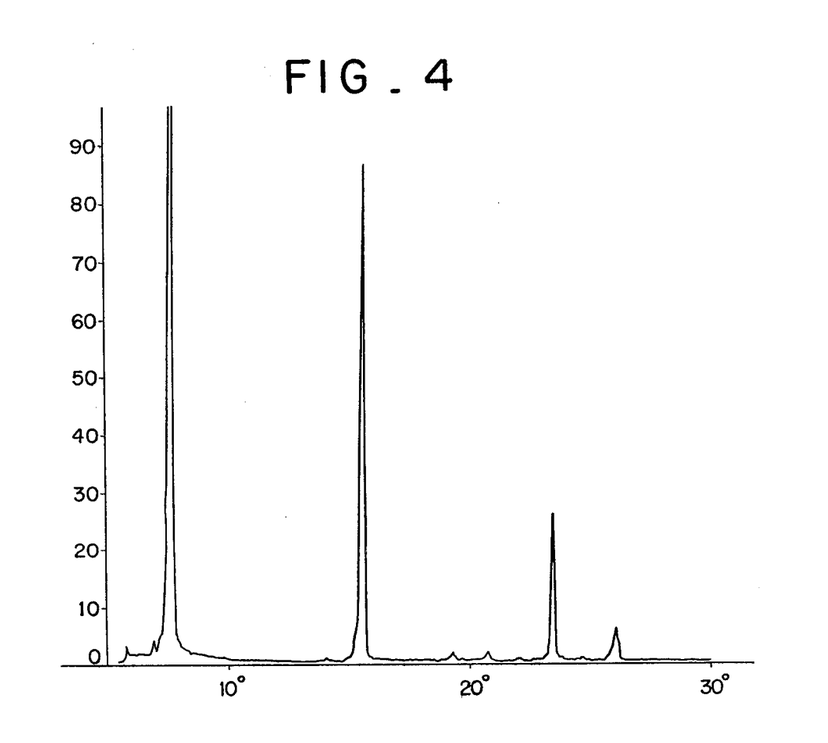
FIG. 4 indicates x-ray diffraction spectrum of slightly water-soluble high molecular weight polymer (B) in a powdery form which is a compound in accordance with the present invention.
Figure 7:
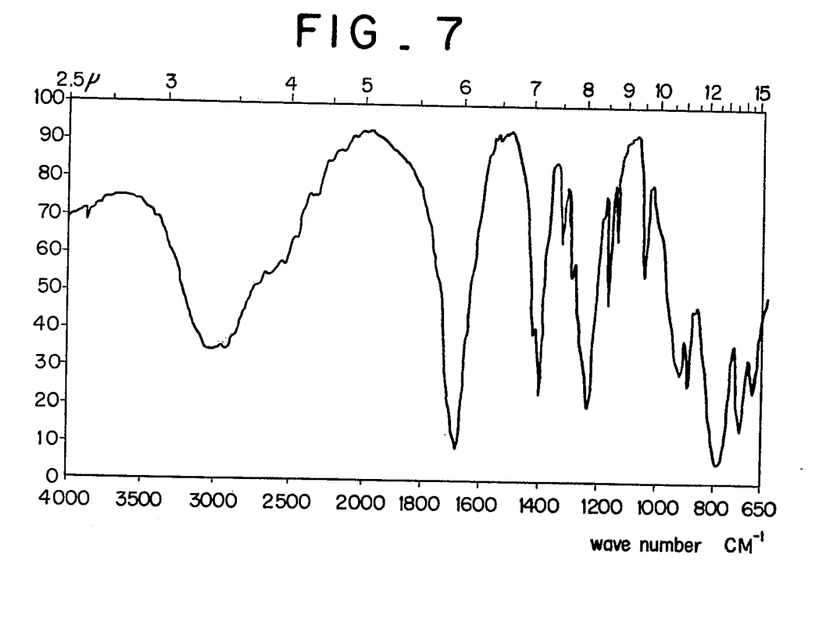
FIG. 7 is an infrared absorption spectrum of the slightly water-soluble high molecular weight polymer (B) which is another compound in accordance with the present invention.

Preparation of high molecular weight polymer (B) of 3-oxygermylpropionic acid:

A suspension of 40 g. of the polymer (A) in 400 ml. of water was settled at room temperature until all needles were changed to heavy bright prisms (it required for 1–3 weeks). After suction, the crystals were taken by filtration and dried under reduced pressure. Thus, 33 g. of white prism high molecular weight polymer (B) which was insoluble in water was obtained. This polymer did not decompose or melt at temperatures below 320° C. and its powder x-ray difraction spectrum as well as infrared absorption spectrum were different from those of the low molecular weight polymer (A). Accordingly, the structure of the polymer (B) was different from that of the polymer (A) (compare FIGS. 4 and 7 indicating powder x-ray diffraction spectrum and infrared absorption spectrum of the high molecular weight polymer (B) with FIGS. 3 and 6 indicating powder x-ray diffraction spectrum and infrared absorption spectrum of the low molecular weight polymer (A)).

EXAMPLE 4

Isolation of germanium chloride-phosphoric acid complex:

As shown in Example 1, a solution obtained by the reaction of germanium dioxide and hypophosphorous acid in conc. hydrochloric acid was poured into 3 l. of cold water while shaking, whereby a white solid germanium chloride-phosphoric acid complex was precipitated out. By suction-filtration, the solid was collected, washed with acetone and then dried under reduced pressure. It is recommended to avoid water-washing since the solid is colored when washed with water.

From 1 mol. (104.6 g.) of germanium dioxide, 136 g. of the complex was obtained. It is assumed that the complex would be a complex of chlorogermanium ($Ge^{II}$ or $Ge^{IV}$) and phosphoric acid. The complex is an effective reagent for synthesis of germanium-containing organic compounds.

EXAMPLE 5

Another preparation of organic trichlorogermyl compound from germanium chloride-phosphoric acid complex:

The complex isolated in Example 4 was suspended in a solvent such as ethanol, methanol, dichloromethane, chloroform, carbon tetrachloride, ether, or the like. The suspension was saturated under ice cooling by blowing dry hydrogen chloride thereinto. When water was employed, conc. hydrochloric acid was used. The complex gradually disappeared at the same time when hydrogen chloride was blown in the system and a completely transparent solution was formed depending upon solvent. The unsaturated compound represented by the formula (I) was added to the system in an equimolar amount. The mixture was warmed (40°–60° C.) for 1 hr. After post-treatment, the corresponding organic trichlorogermyl compound of the formula (II) was obtained.

In the case of the unsaturated compound (I) to which hydrogen chloride was easily added, the aforementioned treated solution of the complex was provided for use after previously heating the solution at 40°–60° C. for 1 hr. and removing an excess of hydrogen chloride from the system. The corresponding organic trichlorogermyl compounds (II) were thus obtained as shown in the table below:

| Strating Material (Compound of the formula (I)) | Product (Compound of the formula (II)) | Yield (%) |
| --- | --- | --- |
| $CH_2=CHCOOH$ | $Cl_3GeCH_2CH_2COOH$ | 80 |
| $CH_2=CHCOOC_2H_5$ | $Cl_3GeCH_2CH_2COOC_2H_5$ | 58 |

EXAMPLE 6

Preparation of trichlorogermyl organic acid ester:

Of a variety of organic trichlorogermyl compounds obtained in Examples 1 and 5, the trichlorogermyl organic acids were esterified.

Esters could be obtained by dissolving various trichlorogermyl organic acids into a solvent such as methanol, ethanol, or the like, saturated with hydrogen chloride, and then reacting at temperatures of 0°–60° C. for 2-3 hrs. For example, ethyl-3-trichlorogermyl propionate was obtained in yield of 90% by treating as described above (b.p. 94° C./5 mmHg).

EXAMPLE 7

The organic trichlorogermyl compound shown in the middle column of the table of Example 1, the organic trichlorogermyl compound shown in the middle column of the table in Example 5 and the trichlorogermyl organic acid ester obtained in accordance with Example 6 were treated according to Examples 2 and 3. Thus, the corresponding low molecular weight polymer and high molecular weight polymer were obtained.

TABLE 1

| Case No. | Sex | Age | Blood pressure before treatment | after 21 days | after 42 days | after 63 days | after 84 days | after 105 days | after 126 days | Final body weight | heart weight |
| --- | --- | --- | --- | --- | --- | --- | --- | --- | --- | --- | --- |
| Control group | | | | | | | | | | | |
| 1 | male | 6 months | 210 | 195 | 206 | 215 | 213 | 205 | 208 | 334 g | 1.57 g |
| 2 | " | " | 183 | 180 | 190 | 198 | 190 | 185 | 192 | 338 | 2.24 |
| 3 | " | " | 182 | 176 | 177 | 183 | 191 | 195 | 193 | 333 | 1.82 |
| 4 | " | " | 184 | 188 | 188 | 190 | 189 | 190 | 196 | 354 | 1.76 |
| 5 | " | " | 215 | 210 | 207 | 216 | 215 | 218 | 212 | 362 | 1.84 |
| 6 | " | " | 183 | 190 | 192 | 191 | 192 | 200 | 198 | 350 | 1.76 |
| 7 | " | " | 195 | 193 | 184 | 196 | 190 | 193 | 201 | 368 | 1.88 |
| average | | | 193 | 190 | 192 | 198 | 197 | 198 | 200 | 348 | 1.83 |
| Treated group | | | | | | | | | | | |
| 8 | " | " | 200 | 200 | 172 | 138 | 131 | 142 | 167 | 371 | 1.84 |
| 9 | " | " | 192 | 195 | 166 | 182 | 126 | 161 | 153 | 356 | 1.68 |
| 10 | " | " | 194 | 190 | 178 | 156 | 145 | 136 | 172 | 330 | 1.39 |
| 11 | " | " | 195 | 195 | 189 | 188 | 148 | 176 | 157 | 331 | 1.46 |
| 12 | " | " | 211 | 198 | 194 | 164 | 146 | 161 | 146 | 289 | 1.50 |
| 13 | " | " | 192 | 190 | 177 | 159 | 162 | 166 | 153 | 332 | 1.51 |
| 14 | " | " | 206 | 198 | 182 | 167 | 170 | 168 | 160 | 328 | 1.65 |
| average | | | 198 | 195 | 179 | 147 | 146 | 158 | 158 | 333 | 1.57 |

What is claimed is:

1. A germanium-containing organic polymer represented by the formula:

$$(\equiv GeCH-CH-COZ)_nO_{1.5n} \quad (III)$$

or

$$(-O-Ge-CH-CH-COZ)_n \quad (IV)$$
(with OH, A, B substituents)

wherein A represents a hydrogen atom, an alkyl group having 1 to 3 carbon atoms, —COOH, —COOR (wherein R is an alkyl group having 1 to 3 carbon atoms), B represents a hydrogen atom or an alkyl group having 1 to 3 carbon atoms; Z represents a hydroxy group, an alkoxy group having 1 to 3 carbon atoms or an alkyl group having 1 to 3 carbon atoms; and n is an integer greater than 3, inclusive.

2. The germanium-containing organic polymer as claimed in claim 1 wherein said A is a hydrogen atom, a methyl group, —COOH,

B is a hydrogen atom or a methyl group; and Z is a hydroxy group, a methoxy group or a methyl group.

3. The germanium-containing organic polymer as claimed in claim 2 wherein said A is a hydrogen atom, a methyl group or —COOH; B is a hydrogen atom or a methyl group; and Z is a hydroxy group, a methoxy group, an ethoxy group or a methyl group.

4. A process for producing germanium-containing organic polymer represented by the formula (III) or (IV) as given in claim 1 which comprises reacting a halogermanium-phosphoric acid complex obtained by treating germanium dioxide with hypophosphorous acid or a salt thereof in hydrohalogenic acid with a compound (I) represented by the formula:

$$\begin{array}{cc} A & B \\ | & | \\ CH=C-COZ \end{array} \quad (I)$$

wherein A is a hydrogen atom, an alkyl group having 1 to 3 carbon atoms, —COOH, —COOR (wherein R is an alkyl group having 1 to 3 carbon atoms), B is a hydrogen atom or an alkyl group having 1 to 3 carbon atoms and Z is a hydroxy group, an alkoxy group having 1 to 3 carbon atoms or an alkyl group having 1 to 3 carbon atoms, to obtain a compound (II) represented by the formula:

wherein A, B and Z have the same meanings as defined above, and X is a halogen atom; and then dissolving said compound (II) in an organic solvent and adding water to the solution thus obtained so as to obtain a white needle crystalline polymer.

5. The process for producing the germanium-containing organic polymer as claimed in claim 4 wherein said compound of the formula (I) wherein A is a hydrogen atom, a methyl group, —COOH, B is a hydrogen atom or a methyl group, and Z is a hydroxy group, a methoxy group or a methyl group, is employed.

6. The process for producing the germanium-containing organic polymer as claimed in claim 5 wherein said compound of the formula wherein A is a hydrogen atom, a methyl group or —COOH; B is a hydrogen atom or a methyl group; and Z is a hydroxy group, a methoxy group, an ethoxy group or a methyl group, is employed.

7. The process for producing the germanium-containing organic polymer as claimed in claim 4 wherein a germanium-containing organic low molecular weight polymer is prepared by dissolving said compound of the formula (II) in acetone or other solvent miscible with water and pouring water into the resulting solution.

8. The process for producing the germanium-containing organic compound as claimed in claim 4 wherein a germanium-containing organic high molecular weight polymer is obtained by settling a suspension of a germanium-containing organic low molecular weight polymer in a small amount of water, said germanium-containing organic low molecular weight polymer being obtained by dissolving the compound of the formula (II) in acetone or other solvent miscible with water and pouring water into the resulting solution.

* * * * *

UNITED STATES PATENT AND TRADEMARK OFFICE
CERTIFICATE OF CORRECTION

PATENT NO. : 4,271,084

DATED : June 2, 1981

INVENTOR(S) : Akira Ishikawa et al.

It is certified that error appears in the above—identified patent and that said Letters Patent is hereby corrected as shown below:

Column 6, line 17, "our" should read -- out --.

Signed and Sealed this

Fifteenth Day of September 1981

[SEAL]

Attest:

GERALD J. MOSSINGHOFF

Attesting Officer

Commissioner of Patents and Trademarks